US011874188B2

(12) United States Patent
Devi Das et al.

(10) Patent No.: US 11,874,188 B2
(45) Date of Patent: Jan. 16, 2024

(54) SELF-DIAGNOSTIC RESINS AND RELATED FIBER COMPOSITES

(71) Applicant: ELANTAS EUROPE S.R.L., Collecchio (IT)

(72) Inventors: Anjali Devi Das, Parma (IT); Enrico Dalcanale, Parma (IT); Roberta Pinalli, Fidenza (IT); Paola Gherardi, Parma (IT)

(73) Assignee: ELANTAS EUROPE S.R.L., Collecchio (IT)

( * ) Notice: Subject to any disclaimer, the term of this patent is extended or adjusted under 35 U.S.C. 154(b) by 424 days.

(21) Appl. No.: 17/423,560

(22) PCT Filed: Feb. 6, 2020

(86) PCT No.: PCT/EP2020/052936
§ 371 (c)(1),
(2) Date: Jul. 16, 2021

(87) PCT Pub. No.: WO2020/165011
PCT Pub. Date: Aug. 20, 2020

(65) Prior Publication Data
US 2022/0113205 A1    Apr. 14, 2022

(30) Foreign Application Priority Data
Feb. 12, 2019 (EP) .................................. 19156705

(51) Int. Cl.
*G01L 1/25* (2006.01)
*C07C 245/08* (2006.01)
(Continued)

(52) U.S. Cl.
CPC .............. *G01L 1/25* (2013.01); *C07C 245/08* (2013.01); *C07D 307/91* (2013.01);
(Continued)

(58) Field of Classification Search
CPC ....... G01L 1/25; G01L 5/0047; C07C 245/08; C07D 307/91; C07D 491/06;
(Continued)

(56) References Cited

U.S. PATENT DOCUMENTS 8,486,708 B2 * 7/2013 Zang .................. G01N 21/6428
977/788
8,986,842 B2 * 3/2015 Frauenrath ............ C09B 69/109
427/407.1
(Continued)

FOREIGN PATENT DOCUMENTS

CN         104819970 A   *  8/2015
EP         2693204 A1    *  2/2014    .......... G01M 5/0033
(Continued)

OTHER PUBLICATIONS

Hanna Traeger, Derek J. Kiebala, Christoph Weder, and Stephen Schrettl: From Molecules to Polymers—Harnessing Inter-and Intra-molecular Interactions to Create Mechanochromic Materials: Nov. 16, 2020, https://doi.org/10.1002/marc.202000573, Wiley Online Library (Year: 2020).*
(Continued)

*Primary Examiner* — Francis C Gray
(74) *Attorney, Agent, or Firm* — Fitch, Even, Tabin & Flannery LLP

(57) ABSTRACT

The present invention relates to the sector of self-diagnostic composite materials. In particular, the invention presents an agent, which can be cross-linked together with a curing agent in a matrix, e.g. an epoxy resin, and fibres, e.g., carbon fibre, in order to obtain a composite material containing a reporting probe capable of detecting stress, fatigue and microscopic cracks in the material with high spatial resolution and sensitivity.

14 Claims, 3 Drawing Sheets

(51) Int. Cl.
*C07D 307/91* (2006.01)
*C07D 491/06* (2006.01)
*C08K 5/1535* (2006.01)
*C08K 5/23* (2006.01)
*C08K 5/3437* (2006.01)

(52) U.S. Cl.
CPC .......... *C07D 491/06* (2013.01); *C08K 5/1535* (2013.01); *C08K 5/23* (2013.01); *C08K 5/3437* (2013.01)

(58) Field of Classification Search
CPC ...... C08K 5/1535; C08K 5/23; C08K 5/3437; G01M 5/0033; G01M 5/0091; B60T 2220/03; B60T 8/17558; G01N 31/22; G01N 21/6428; G01N 21/77; G01N 33/442
See application file for complete search history.

(56) References Cited

U.S. PATENT DOCUMENTS

| | | | |
|---|---|---|---|
| 9,823,193 B2 * | 11/2017 | Zang | C07D 471/06 |
| 2010/0197039 A1 * | 8/2010 | Zang | C07D 491/06 |
| | | | 428/397 |

FOREIGN PATENT DOCUMENTS

| | | | | |
|---|---|---|---|---|
| FR | 2900408 A1 * | 11/2007 | ............. | C08G 77/12 |
| WO | WO-2007125043 A1 * | 11/2007 | ............. | C08G 77/12 |

OTHER PUBLICATIONS

O. Rifaie-Graham et al., "Self-Reporting Fiber-Reinforced Composites That Mimic the Ability of Biological Materials to Sense and Report Damage," Adv. Mater. 2018, 1705483.

E. A. Appel et al., "Decoupled Associative and Dissociative Processes in Strong yet Highly Dynamic Host-Guest Complexes," J. Am. Chem. Soc., 2017, 139, 12985-12993.

F. Biedermann et al., "Strongly Fluorescent, Switchable Perylene Bis(diimide) Host-Guest Complexes with Cucurbit[8]uril In Water," Angew. Chem. Int. Ed., 2012, 51, 7739-7743.

E. A. Appel et al., "The control of cargo release from physically crosslinked hydrogels by crosslink dynamics," Biomaterials, 35 (2014) 9897-9903.

Y.P. Li et al., "Study on the inclusion interactions of berberine hydrochloride and cucurb[7] by spectrofluorimetry," Chinese Chemical Letters, 20 (2009) 322-325.

C. Marquez et al., "Cucurbiturils: Molecular Nanocapsules for Time-Resolved Fluorescence-Based Assays," IEEE Transactions on Nanobioscience, vol. 3, No. 1, Mar. 2004, 39-45.

A. E. Früh et al., "Strain Field Self-Diagnostic Poly(dimethylsiloxane) Elastomers," Chem. Mater., 2017, 29, 7450-7457.

M. Porel at al., "Interaction Between Encapsulated Excited Organic Molecules and Free Nitroxides: Communication Across a Molecular Wall," Langmuir, 2011, 27, 10548-10555.

International Search Report and Written Opinion for International Application No. PCT/EP2020/052936 dated May 6, 2020 (9 pages).

* cited by examiner (a)

(b)

(c)

(a)

(b)

(a)

(b)

SELF-DIAGNOSTIC RESINS AND RELATED FIBER COMPOSITES

The present invention relates to the sector of self-diagnostic composite materials. In particular, the invention presents an agent, which can be cross-linked together with a curing agent in a matrix, e.g. an epoxy resin, and fibres, e.g., carbon fibre, in order to obtain a composite material containing a reporting probe capable of detecting stress and microscopic cracks in the material with high spatial resolution and sensitivity.

BACKGROUND OF THE INVENTION

Composites are desirable materials for high-performance applications, due to their affordable price, light weight and processability. However, microscopic damages, which are difficult to detect, can compromise the mechanical integrity of the material and subsequently lead to catastrophic failure. The capability to monitor the maximum volumetric strain that has occurred in the element during service enables optimisation of design and enhancement of safety levels. The availability of a detection tool to identify highly volumetric strained regions without the need of any complex measurement device and without interacting with the microstructure bearing mechanism of the material is therefore highly desirable.

The current strategy to ensure safety in materials used in applications where structural integrity is absolutely crucial, such as the aerospace industry comprise three main approaches. 1) The use of a large surplus of material, 2) Replacement of components at regular intervals regardless of state of integrity, and 3) Non-Destructive Evaluation (NDE) or Non-Destructive Testing (NDT). NDT refers to evaluation and inspection process of materials without altering or harming the object being tested and provides a cost effective means of testing. Current methods of NDT involve X-ray, lock in thermography, pulse echo ultrasounds methods, which can locate defects in homogenous materials. The drawback of current NDE's is that they require high skill levels and repeated testing against test samples for accuracy, and involve expensive monitoring equipment.

In the context of non-destructive testing, materials that are able to autonomously sense their state and report damage via fluorescence or visual color changes have therefore become increasingly important.

However, the main disadvantage of the methods known in the art is that they require either a large amount of reporting system (>=10%) or bulk changes to the polymer backbone, both of which compromise the physical properties of the pristine commercially available polymers specifically suited to certain applications.

Früh et al. describe a host guest additive based on a tetraphosphonate cavitand as a host and N-methylated pyridinium salt as a guest. This host guest additive can be included in a flexible elastomer in a quantity lower than 0.1 weight % imparting self-diagnostic properties. In addition to detecting fracture, it also allows to detect areas of high volumetric strain in the matrix, thereby predicting areas prone to damage. (Früh, Artoni, Brighenti, & Dalcanale, 2017).

Also described in the literature are host guest systems based on cucurbiturilis. Cucurbiturils are a family of versatile host molecules that have been shown to form ternary complexes that can quench fluorescent molecules on binding with an additional guest. The fluorescence reappears on dissociation of the complex. (Biedermann, Elmalem, Ghosh, Nau, & Scherman, 2012).

Further, the use of these systems is described as a probe to investigate the release characteristics of a hydrogel matrix (Appel et al, Biomat, vol 35, no. 37, 16 Sep. 2014, 9897-9903)

However, these latter documents are silent about the possibility to use these kind of complexes in composite materials or in thermosetting polymers or as a probe to detect defects in a material.

Accordingly, there is a need to find new chemical systems, which allow to detect defects in thermosetting polymers, preferably in composite materials, without altering the properties of the material as such.

SUMMARY OF THE INVENTION

The above-mentioned problems are solved by the agent of the invention. In fact, the present invention relates to an agent to detect stress or fatigue in a composition comprising:
  a. Cucurbituril[8];
  b. a fluorescent compound having an emission at wavelength above 400 nm;
  c. a quencher compound;
wherein the fluorescent compound and the quencher compound have both at least one reactive groups each of which group can be the same or different and is selected from —OH, a primary or a secondary amine and carboxylic anhydride.

Preferably, the fluorescent compound and the quencher compound of the agent have both one, two, three or four reactive groups, which can be the same or different, most preferably one or two reactive groups, most preferably one reactive group.

In a preferred embodiment, the reactive group of the fluorescent compound and the quencher compound can be the same or different and is selected from a primary or a secondary amine.

In a preferred embodiment, the elements a., b. and c. are in the form of a ternary complex.

A complex is a molecular entity formed by a loose association involving two or more component molecular entities (ionic or uncharged), or the corresponding chemical species. The bonding between the components is normally weaker than in a covalent bond.

The agent preferably encompasses uncharged molecular entities.

Within the meaning of the invention, the agent is in a form of a ternary complex, preferably having uncharged compounds as fluorescent and quencher compounds. A further advantage of the agent of the invention is that it can be added in a composition at a very low concentration, for example of $10^{-6}$ mol kg$^{-1}$.

In a preferred embodiment of the invention, the amount of the agent in a composition comprising the agent is preferably at least $10^{-6}$ mol kg$^{-1}$, preferably, the amount is in the range of $10^{-6}$ to $10^{-4}$ mol kg$^{-1}$, more preferably, the amount is in the range of $10^{-6}$ to $10^{-5}$ mol kg$^{-1}$. The agent of the invention overcomes the limits of currently available self-diagnostic materials by providing a non-invasive diagnostic method based on fluorescence detection to identity microfractures and areas of high strain and fatigue, for example, in carbon fiber epoxy composite materials. It is based on an agent comprising Cucurbituril[8], also defined as CB[8], which is a host molecule capable of binding two guests, one fluorescent compound and a quencher compound. This agent together with a curing agent having the same reactive groups can cross-link to polymer chains and selectively dissociates on application of stress, thereby providing a fluorescent response.

Selectively dissociates on application of stress means that the weaker bonds of the agent breaks before the covalent bonds of the material. The agent of the present invention can be seen as a damage reporting element as a host guest complex, engineered to cross link a resin, such as epoxy chains. The complex dissociates under mechanical stress, leading to the turn on of fluorescence.

Turn-on fluorescence, which is easily detectable with hand-held equipment, offers an excellent contrast between affected and unaffected regions, providing a very sensitive tool for the monitoring of structural elements. Since very small quantities of these reporting systems are needed, the physical properties of the final material, for example the resulting self-diagnostic composite, are not altered compared to the pristine material. This allows the incorporation of the reporting system into commercial resins, such as epoxy resins, rendering them self-diagnostic without compromising bulk properties.

Fluorescence is the emission of light by a substance that has absorbed light or other electromagnetic radiation. It is a form of luminescence. In most cases, the emitted light has lower energy, and therefore longer wavelength than the absorbed radiation. The most striking example of fluorescence occurs when the absorbed radiation is in the ultraviolet region of the spectrum, and thus invisible to the human eye, while the emitted light is in the visible region, which gives the fluorescent substance a distinct color that can be seen only when exposed to UV light. Fluorescent materials cease to emit visible light nearly immediately when the radiation source stops.

UV light has a wavelength between 10 nm and 380 nm.

Fluorescent compounds means those compounds, which emit above 400 nm. More preferably, are those compounds which emit in the range between 400 nm and 700 nm.

Quenching refers to any process which decreases the fluorescence intensity of a given substance. A variety of processes can result in quenching, such as excited state reactions, energy transfer, complex-formation and collisional quenching.

The agent of the invention is preferably a ternary complexes of Cucurbituril[8], also described as host, and the fluorescent and quencher compounds as guests.

When the fluorescent and the quencher compounds (guest molecules) are in the form as a ternary complex with Cucurbituril[8], the system is non fluorescent because the fluorescent compound interacts with the quencher compound. To ensure that there is no fluorescence observed in a system when no external stress is applied, a molar excess of the quencher compound should be present, with respect to equimolar amounts of the fluorescent compound and Cucurbituril[8]. In one embodiment, a 5-fold molar excess of the quencher compound is present with respect to equimolar amounts of the fluorescent compound and Cucurbituril[8], in a further embodiment a 10-fold molar excess of the quencher compound is present.

The formed complex is stable in the polymer matrix, such as the epoxy matrix, under conditions of curing.

The choice of the fluorescent compound is made taking into consideration the transparency window of commercial epoxy resins and both guest molecules are functionalized with groups, preferably end groups, which allow to crosslink the agent in a polymer matrix. For example, the agent can be functionalized with amine groups in order to crosslink with the epoxy group of the resin.

In a preferred embodiment the fluorescent compound is a compound of formula (I)

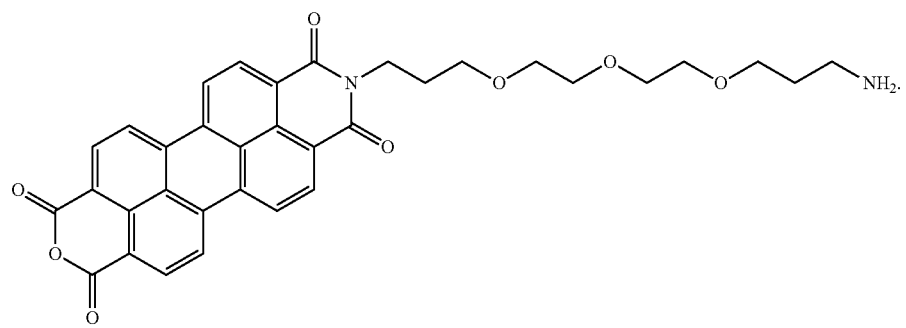

(I)

In a preferred embodiment, the quencher compound is selected from a compound of formula (II) or (III),

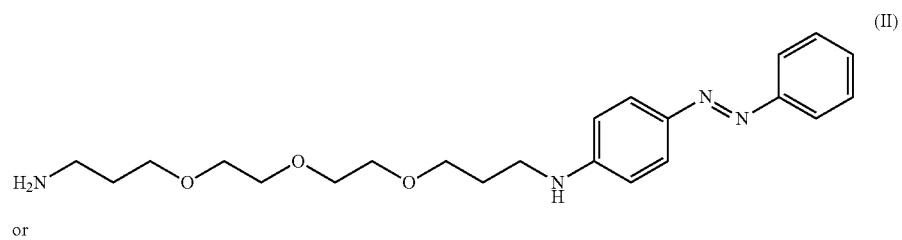

(II)

or

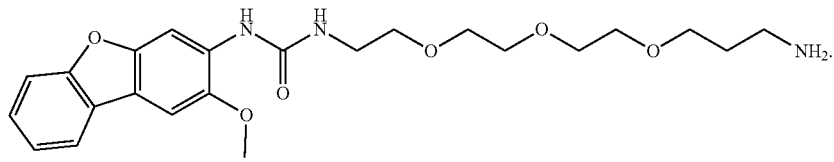

(III)

Figure 1:
FIG. 1 (a) shows images at the fluorescence microscope of an untested specimen (b) a specimen stressed at 70% Tm (ultimate tensile strength) (b) and broken specimen (all at 10× magnification).
Figure 1:
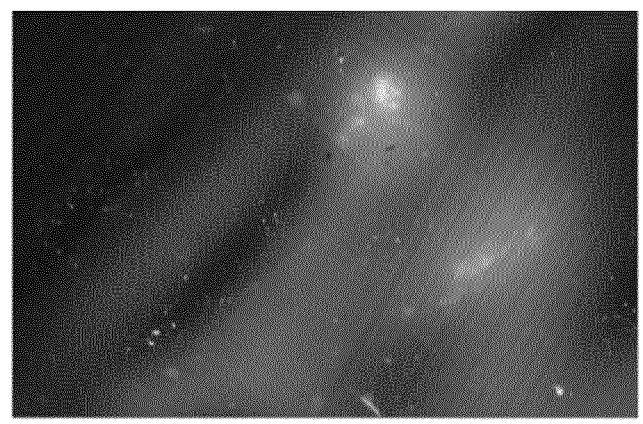
Figure 1:
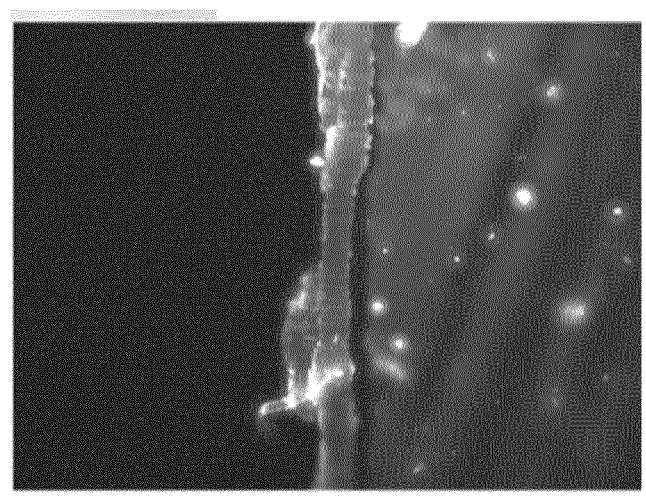

In a further embodiment, the invention relates to a composition comprising the agent, a resin and a curing agent, wherein the curing agent comprises the same reactive groups as the agent and the resin comprises groups that react with the reactive groups of the agent and of the curing agent.

Preferably, the resin comprises epoxy groups or hydroxyl or polyhydroxyl and isocyanate groups.

Further, the invention relates to a cured composition obtained by reacting the composition of the invention.

Preferably, the cured composition comprises secondary or tertiary amines or mixtures thereof.

The cured composition further comprises one or more fibres.

In another embodiment, the cured composition is in the form of an article.

Within the meaning of the invention, article is any three dimensional object, which can be made using the agent of the invention and a thermosetting polymer. In a preferred embodiment, the article comprises the cured composition of the invention. In another embodiment, the invention relates to a process for producing a cured composition, characterized in that the cured composition comprises agent of the invention.

In another embodiment, the invention relates to the use of the agent in a composite materials, preferably to detect at least one of stress and fatigue in a composite materials.

In another embodiment, the invention relates to the use of the agent in a thermosetting polymer, preferably to detect at least one of stress and fatigue in a thermosetting polymer.

In another embodiment, the invention relates to the use agent to detect stress and fatigue in epoxy resin composites.

In a preferred embodiment, the composition of the invention comprises an epoxy resin having an epoxide equivalent weight between 100 and 1000 g/mol, preferably between 150 and 550 g/mol, more preferably between 160 and 400 g/mol, most preferably between 165 and 350 g/mol.

In a preferred embodiment, the curing agent of the composition of the invention has at least two reactive groups selected from —OH, a primary or a secondary amine and carboxylic anhydride, preferably, the reactive groups are selected from a primary or a secondary amine Preferred curing agent of the composition of the invention is selected from the same group or from different groups consisting of aliphatic amines, cycloaliphatic amines, heterocyclic amines, aromatic amines, polyetheramines, polyaminoamides and the adducts thereof with epoxy groups containing compounds. More preferably poly(propylene glycol) bis(2-aminopropyl ether) with different molecular weights, trimethylolpropane tris[poly(propylene glycol), amine terminated] ether, 2(1-piperazinyl)ethylamine, 3-aminomethyl-3,5,5-trimethylcyclohexylamine, 3,6,9,12-tetraazatetradecane-1,14-diamine, tetraethylenepentamine and triethylenetetramine, 3,6-diazoctanethylenediamine, 3,6,9-triazaundecamethylenediamine, 1,3-bis(aminomethyl)benzene, 1,3-bis(aminomethyl)cyclohexane, 5-diethyl toluene-2,4-diamine and 3,5-diethyl toluene-2,6-diamine (mixture of the two isomers), 2,2'-(ethylenedioxy)bis(ethylamine), 1,6-diamino-2,2,4(2,4,4)-trimethylhexane, N'-(3-aminopropyl)-N,N-dimethylpropane-1,3-diamine, 4,4'-diaminodicyclohexylmethane, 1,2-cyclohexanediamine and dicyandiamide mixtures thereof.

Further preferred curing agents can be selected from the group consisting of the previously cited amines partially reacted with epoxy derivatives in excess of amines, also known as adducts, to introduce an OH functionality in the structure to control vapor pressure, reactivity and final properties. Preferably adducts are not cross linked.

Further preferred curing agents can be selected from the group of anhydrides preferably selected from the group consisting of methyl-5-norbornene-2,3-dicarboxylic anhydride, 4-methyl-1,2-cyclohexanedicarboxylic anhydride (mixtures of cis and trans), dodecenyl succinic anhydride (mixtures of isomers), tetrahydrophthalic anhydride, tetrahydromethylphthalic anhydride, hexahydrophthalic anhydride and mixtures thereof, alone or together with catalysts such as Lewis bases or acids, tertiary amines such as benzyldimethylamine, dimethylaminomethylphenol, tris(dimethylaminomethyl)phenol, boron tri halide amine complexes, stannic chloride, ammonium salts, phosphonium salts, and substituted imidazoles.

Within the meaning of the invention, curing agents and hardeners have the same meaning and are in principle any of those known in the art for the curing of epoxies. In one embodiment, the curing agents are used in a stoichiometric ratio, with respect to the epoxy groups present in the resin. This means that the ratio of the amount of the epoxy groups in the composition and the amount of the active hydrogen linked to an amine nitrogen of the amine functional group are 100 to 100.

In another embodiment, the ratio of the amount of the epoxy groups in the composition and the amount of the active hydrogen linked to an amine nitrogen of the amine functional group are 100 to 130, preferably of 100 to 120, more preferably of 100 to 110.

In another embodiment, the ratio of the amount of the epoxy groups in the composition and the amount of the active hydrogen linked to an amine nitrogen of the amine functional group are 130 to 100, preferably of 120 to 100, more preferably of 110 to 100.

In another embodiment, the composition of the invention further comprises at least one additive. Preferred additives are plasticizers, toughening agents, fillers and nanofillers, adhesion promoters, rheological agents, pigments, reinforcing aids, catalysts, UV and thermal protectors.

In another embodiment, the composition of the invention further comprises at least one inorganic filler. Preferred inorganic filler are calcium carbonate, silica and silicates, glass microspheres, alumina hydrates, hollow microspheres, chopped fibres.

In another embodiment, the composition of the invention further comprises at least one organic filler. Preferred organic filler are phenolic and acrylic microspheres, low profile additives, toughening agents and rubbers.

In a preferred embodiment of the invention, the curing step is performed for a time comprised between 1 minute and 72 hours, preferably between 20 minutes and 8 hours.

In another preferred embodiment of the invention, the curing step is performed at a temperature comprised between 15 and 200° C., preferably, between 25 and 150° C., preferably between 30 and 120° C.

Preferably, the cured composition comprises a thermosetting polymer. Preferred thermosetting polymers are selected from the group consisting of epoxy, polyester, polyurethanes, phenolic, polyaminoamides, polyamideimide and silicone based resins. Most preferred thermosetting polymers are crosslinked epoxy resins and polyurethanes.

Preferred resins of the invention are those resins, which react with the reactive groups of the agent and of the curing agent and result in the thermosetting polymer as defined herein.

Within the meaning of the invention, the thermosetting polymer results from the curing of the resin with the curing agent and the agent of the invention.

In a preferred embodiment, the article is a composite material, for example a combination of a thermosetting polymer and fibres.

The composite material is obtained with all known technologies like RTM, autoclave, stratification, infusion, poltrusion, filament winding.

Preferably, the fibres used in the composite material are selected from carbon fibres, glass fibres, aramid fibres, natural or synthetic fibres and mixtures thereof. Most preferred are carbon fibres alone or mixed with one or more further fibres. Most preferably, the fibres are carbon fibres alone or mixed with Kevlar.

EXAMPLES

List of the commercially available compounds

| Name of the Compound | Available by |
| --- | --- |
| Cucurbituril[8] (CB[8]) | Sigma Aldrich |
| EC157 - Epoxy resin | ELANTAS Europe Srl |
| W152LR - Formulated polyetheramines | ELANTAS Europe Srl |
| Carbon fibre fabrics - | Delta Preg Srl |

If not otherwise specified, the starting material and intermediates are commercially available.

1) Design of the Agent

The present invention has been realised by the design and synthesis of the agent as exemplified here below. Non-limiting examples of the fluorescent and quencher compounds for the complexes have been designed and synthesised as described herein below, while the host CB[8] is a commercially available compound.

The structures and description of the components of the agents are shown in Table 1.

TABLE 1

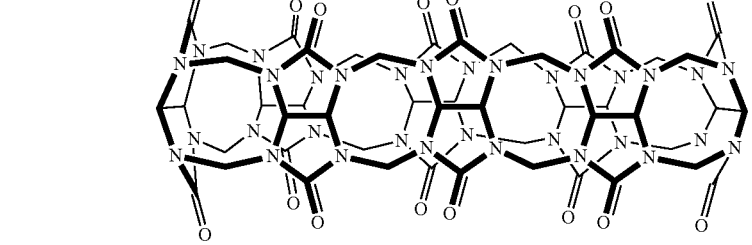

TABLE 1-continued

| Ex | Name/Chemical Structure |
|---|---|
| Quencher Compound 1 (QC1) | (E)-N-(3-(2-(2-(3-aminopropoxy)ethoxy)ethoxy)propyl)-4-(phenyldiazenyl)aniline 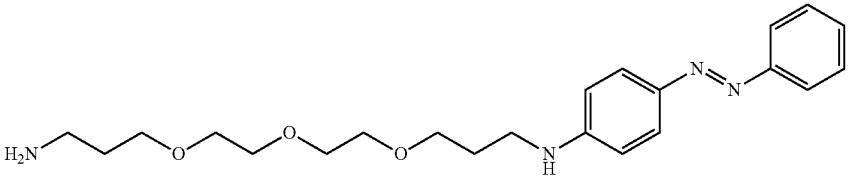 (II) |
| Quencher Compound 2 (QC2) | 1-(3-(2-(2-(3-aminopropoxy)ethoxy)ethoxy)propyl)-3-(2-methoxydibenzo[b,d]furan-3-yl)urea 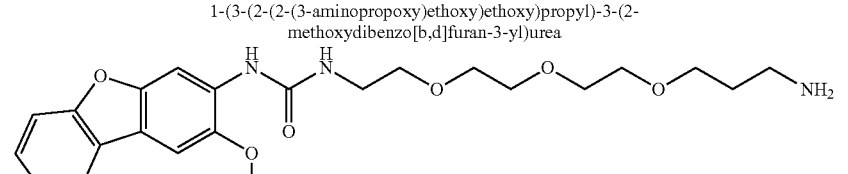 (III) |

2) Synthesis of Fluorescent and Quencher Compounds

2.1) Synthesis of the Fluorescent Compound (FC)

3,4,9,10-Perylenetetracarboxy-3,4-anhydride Potassium Salt 3,4,9,10-Perylenetetracarboxy-3,-anhydride potassium salt was prepared by treating a solution of 3,4:9,10-Perylenetetracarboxydianhydride (10.0 g, 25.5 mmol) in water (800 mL) with KOH (40.0 g, 0.71 mol) and stirring the resulting mixture was stirred at 90° C. for 2 h. Acetic acid (50 mL) was then added and the reaction was stirred at 90° C. for 40 min. The precipitate (10.0 g, 93%) was removed by filtration and washed with methanol before being dried at 120 C.

9-(3-(2-(2-(3-aminopropoxy)ethoxy)ethoxy)propyl)-3,4,9,10-perylene-tetracarboxy-3,4-anhydride-9,10-imide (Fluorescent Compound (FC))

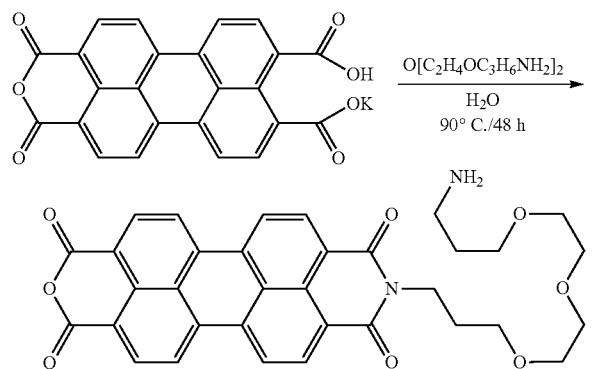

3,4,9,10-Perylenetetracarboxy-3,4-anhydride potassium salt (0.96 g, 2 mmol) and 4,7,10-trioxa-1,13-tridecanediamine (2.37 g, 10 mmol) were placed in a round bottom flask and water (40 mL) was added. The solution was stirred at 90° C. for 48 h before the addition of aqueous potassium carbonate (25 w/w, 100 mL). The solution was heated at 90° C. for 3 h. The solid was filtered off and washed from the filter with a water (150 mL) and triethylamine (5 ml) mixture. The filtrate was diluted with HCl (2 M, 250 mL) and after sitting overnight the precipitated solid was filtered off and washed with methanol. The product was obtained as a solid. (0.77 g, 65%) $^1$H NMR (400 MHz, DMSO-$d_6$) δ: 8.80 (d, J=7.9 Hz, 2H), 8.47 (dd, J=11.7, 8.0 Hz, 2H), 7.75-7.69 (m, 4H), 4.16-4.13 (m, 2H), 3.55-3.43 (m, 4H), 3.09 (dd, J=7.1, 4.9 Hz, 2H), 2.83 (td, J=6.4, 0.6 Hz, 2H), 1.93 (dd, J=7.1, 6.4 Hz, 2H), 1.77 (dd, J=13.2, 6.4 Hz, 2H); MS (ESI) m/z: [M+H]$^+$ calculated for $C_{22}H_{33}N_4O_3$, 595.21; found, 595.36

2.2) Synthesis of the Quencher Compound 1 (QC1)

(E)-1-(4-bromophenyl)-2-phenyldiazene

A solution of $H_2O_2$(35%, 3.3 mL) in 2.7 mL water was added to a suspension of 4-bromoaniline (1 g, 5.81 mmol) in MeOH (1.8 mL). $MoO_3$ (90 mg) and 1N KOH (0.6 mL) was added. The reaction mixture was stirred for 48 h at room temperature, the precipitate was obtained by filtration washed with water and dried to give the 1-bromo-4 nitrosobenzene without further purification. Aniline (41.2 mg, 4.5 mmol) was added to a solution of the above 1-bromo-4nitrosobenzene in acetic acid (60 mL) and the mixture was refluxed for 12 h. The solvent was evaporated and the crude product was purified via column chromatography on silica gel to give (E)-1-(4-bromophenyl)-2-phenyldiazene in 77% yield. $^1$H NMR (300 MHz, CDCl$_3$): δ 7.95-7.92 (dd, 2H), 7.85-7.81 (dd, 2H), 7.70-7.65 (dd, 2H), 7.58-7.53 (dd, 2H), 7.51-7.49 (t, 1H). ESI-MS [M+H]$^+$ m/z calculated for $C_{12}H_9BrN_2$: 261.12; found, 261.00.

(E)-N-(3-(2-(2-(3-aminopropoxy)ethoxy)ethoxy)propyl)-4-(phenyldiazenyl)aniline (Quencher Compound 1 (QC1))

1-(3-(2-(2-(3-aminopropoxy)ethoxy)ethoxy)propyl)-3-(2-methoxydibenzo[b,d]furan-3-yl)urea (Quencher Compound 2 (QC2))

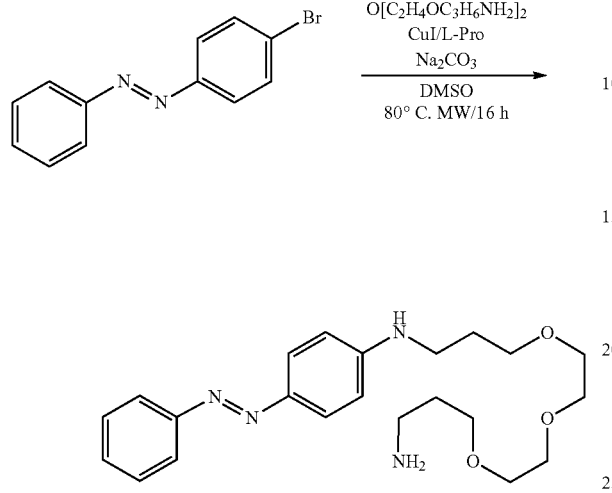

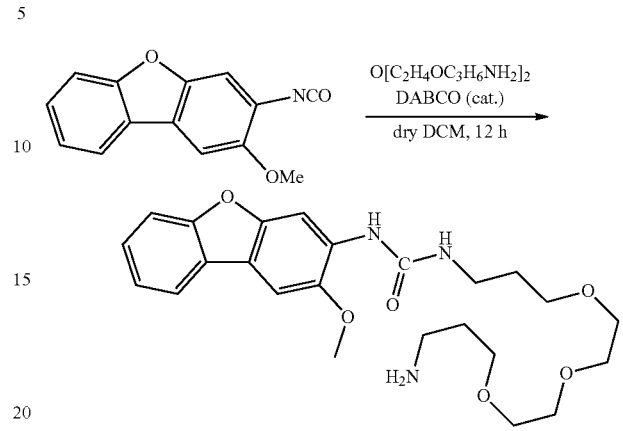

A solution of (E)-1-(4-bromophenyl)-2-phenyldiazene (52 mg, 0.2 mmol), L-proline (46 mg, 0.4 mmol), copper(I) iodide (37 mg, 0.2 mmol), sodium carbonate (31 mg, 0.3 mmol) and 4,7,10-trioxa-1,13-tridecanediamine (1.75 ml, 7.9 mmol) in DMSO (2.3 mL) was heated under microwave irradiation for 16 h at 80° C. DMSO and 4,7,10-trioxa-1,13-tridecanediamine were removed from the reaction mixture and the remaining crude purified by flash chromatography (DCM:MeOH 9:1), yielding a solid (54 mg, 68%). $^1$H NMR (300 MHz, CDCl$_3$) δ: 7.80-7.82 (m, 4H), 7.44-7.49 (m, 2H), 7.36-7.39 (m, 1H), 6.64-6.70 (m, 2H), 3.94 (bs, 4H), 3.31-3.61 (m, 14H), 2.61 (bs, 2H), 1.74-1.01 (m, 4H); MS (ESI) m/z: [M+H]$^+$ calculated for C$_{22}$H$_{33}$N$_4$O$_3$, 401.25; found, 401.26.

2.3) Synthesis of the Quencher Compound 2 (QC2)

3-Isocyanato-2-methoxydibenzo[b,d]furan

A solution of 2-methoxydibenzo[b,d]furan-3-amine (0.5 g, 2.3 mmol) and triethylamine (0.7 mL, 5.2 mmol) in 50 mL anhydrous DCM was cooled to 0° C. under inert atmosphere and treated with triphosgene (1.5 g, 5.2 mmol). The mixture was stirred overnight at room temperature and purified by chromatography over silica gel. The solvent was removed to give the product (0.4 g, 75%) as a solid. $^1$H NMR (400 MHz, CDCl$_3$) δ: 7.90 (d, 1H), 7.57 (d, 1H), 7.48 (m, 1H), 7.38 (m, 2H), 7.25 (s, 1H), 4.03 (s, 3H).

A solution of 2-methoxydibenzo[b,d]furan-3-amine (0.5 g, 2.3 mmol) and triethylamine (0.7 mL, 5.2 mmol) in 50 mL anhydrous DCM was cooled to 0° C. under inert nitrogen atmosphere and treated with triphosgene (1.5 g, 5.2 mmol). The mixture was stirred overnight at room temperature and purified by chromatography over silica gel. The solvent was removed to give the product (0.4 g, 75%) as a solid. $^1$H NMR (400 MHz, CDCl$_3$) δ: 7.90 (d, 1H), 7.57 (d, 1H), 7.48 (m, 1H), 7.38 (m, 2H), 7.25 (s, 1H), 4.03 (s, 3H).

To a solution of 4,7,10-trioxa-1,13-tridecanediamine (1.2 mmol) in dry DCM, a solution of 3-isocyanato-2-methoxydibenzo[b,d]furan (0.14 g, 0.6 mmol) was added dropwise and the mixture was stirred for 48 hours at room temperature in the presence of a catalytic amount of DABCO. The solvent was removed and the product was purified via preparative TLC to give a viscous oil. $^1$H NMR (400 MHz, CDCl$_3$): δ 8.51 (s, 1H), 7.81-7.83 (d, 2H), 7.49-7.51 (m, 2H), 7.29-7.39 (mc, 4H), 4.00 (s, 3H), 3.60-3.71 (m, 10H), 3.40-3.26 (m, 2H), 2.97-3.01 (m, 4H), 1.86-1.92 (m, 4H). m/z: [M+H]$^+$ calcd for C$_{24}$H$_{33}$N$_2$O$_6$, 460.24; found, 460.25.

3. General Procedure for the Transfer of CB[8] Complexes into Epoxy Systems

Aqueous solutions of the components of the ternary complex, at a concentration of $10^{-4}$ mol dm$^{-3}$ for the guests and $10^{-5}$ mol dm$^{-3}$ for the CB[8], were prepared in ultrapure water.

The CB[8] and FC solutions were mixed together in equimolar quantities followed by the addition of QC1 in 100 fold molar excess or QC2 in a 10 fold molar excess. The formation of the ternary complex occurs stepwise and is followed by fluorescence spectroscopy in aqueous solution. Upon formation of the ternary complex with the second guest the emission of the fluorescent guest is drastically reduced with respect to the control sample containing only the fluorescent guest and CB[8]. An excess of the quencher was added to obtain complete quenching of fluorescence.

The final solution was then thoroughly mixed with one of the elements of the thermoset epoxy resin, generally the curing agent. The amount of the components was calculated in order to obtain the desired concentration in the final cured thermoset, $1 \times 10^{-6}$ mol kg$^{-1}$. The obtained emulsion was placed in the oven at 120° C. and homogenized frequently during the evaporation process. Once the water was completely removed, the sample appeared completely transparent. The loaded sample was removed from the oven and cooled to room temperature. The component containing the CB[8] complex is subsequently used for curing the epoxy resin.

Example 3.1

Stock solution of CB[8] at [c]=$1.3 \times 10^{-5}$M, FC at [c]=$1.3 \times 10^{-4}$M and QC1 at $1.3 \times 10^{-2}$ M were prepared in ultrapure water. To 100 ml of CB[8] stock solution, 10 ml of FC stock solution was added. Subsequently 10 ml of QC1 was added to give a solution of ternary complex, with the ratio of components in solution CB[8]:FC:QC1=1:1:100.

This solution was added to 300 g of the hardener W152LR and stirred vigorously while heating 120° C. to remove the water completely. Removal of water was followed by monitoring changes in weight. Once the water was removed, 250 g of the loaded hardener was added to 833 g of the epoxy resin EC 157 to give 1.3 kg of the final resin which is then used for the preparation of the composite material.

Example 3.2

Stock solution of CB[8] at [c]=1.3×10$^{-5}$M, FC at [c]=1.3×10$^{-4}$M were prepared in ultrapure water. To 100 ml of CB[8] stock solution, 10 ml of FC stock solution was added. The above solution was then used to dissolve 2.99 mg of QC2 (Stock solution method was avoided due to low solubility) to give the ternary complex, with the ratio of components in solution CB[8]:FC:QC2=1:1:5.

This solution is added to 300 g of the hardener W152LR and stirred vigorously while heating at 120° C. to remove the water completely. Removal of water was followed by monitoring changes in weight. Once the water was removed, 250 g of the loaded hardener was added to 833 g of the epoxy resin EC 157 to give the final resin which is then used for the preparation of the composite material.

4. General Procedure for the Preparation of Self-Diagnostic Carbon Fiber Epoxy Resin Composite Specimens For the preparation of composite specimens, a commercial epoxy system by Elantas Europe Srl was employed (EC157 epoxy resin and W152LR hardener). The mixing ratio for EC157-W152LR is 100:30 by weight. The appropriate quantity of hardener W152LR containing the ternary complex incorporated via the procedure described in 3 was added to EC157 and mixed carefully. A degassing step under vacuum can be carried out if necessary. The resin cures at room temperature. Specimens were prepared by vacuum infusion into carbon fibre fabric 200 gsm texture twill provided by Delta Preg Srl Example 4.1

The Fabric used was HS 3K Twill 2×2 fabric (200 g/m$^2$) In order to fabricate a Panel of 500×500 mm with a thickness of 3 mm, we used
  833 g of component A EC157
  250 g of component B W152LR (Curing agent loaded with QC1)
  12 sheets of Carbon fiber fabric weighing 200 g
  833 g of EC157, epoxy resin, and 250 g of the loaded W152LR hardener were mixed together according to the mixing ratio for EC157-W152LR is 100:30 by weight. Specimens were prepared by vacuum infusion into carbon fiber fabric at room temperature of 25° C. for 24 h.

Example 4.2

The same procedure of Example 4.1 was repeated using the curing agent loaded with QC2 instead of QC1.

5. Testing of Self-Diagnostic Composites

Specimens were tested in accordance with American Society for Testing and Materials (ASTM) standards. Samples were imaged under fluorescence microscope to assess self-diagnostic properties.

5.1 Tensile Testing Under ASTM D3039

Specimens were subject to tensile testing using MTS Insight Electromechanical Testing Systems 150 kN, with 250 kN hydraulic grips at 2 mm/min (Grip pressure: 100 bar) following the ASTM D3039 method. This test method is designed to produce tensile property data for material specifications, research and development, quality assurance, and structural design and analysis. The method determines the in-plane tensile properties of polymer matrix composite materials reinforced by high-modulus fibres. Tested and untested specimens were then studied under a fluorescence microscope, where specimens subject to strain showed a significant increase in brightness (FIG. 1).

5.2 Compression Testing Under ASTM D3410

Figure 2:
FIG. 2 (a) shows images at the fluorescence microscope of an untested specimen (b) and a broken specimen (all at 10× magnification).
Figure 2:
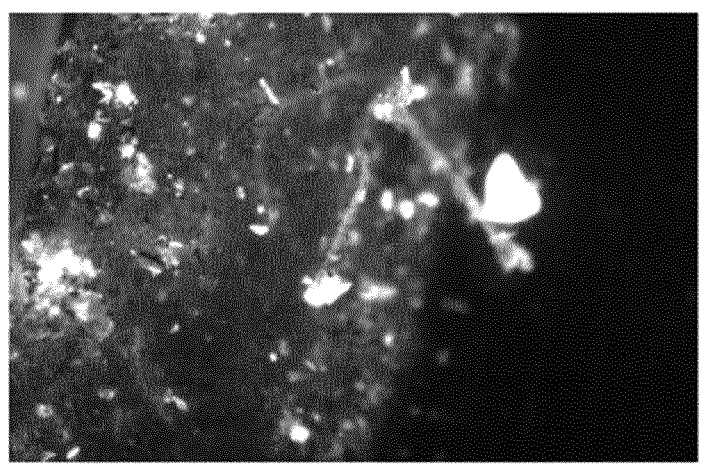

Specimens were subject to compression testing using MTS Insight Electromechanical Testing Systems 150 kN, with 250 kN hydraulic grips at 2 mm/min (Grip pressure: 100 bar) following the ASTM D3410 method. This test method determines the in-plane compressive properties of polymer matrix composite materials reinforced by high-modulus fibres. Tested and untested specimens were then studied under a fluorescence microscope, where specimens subject to strain showed a significant increase in brightness (FIG. 2).

5.3 Fatigue Testing Under ASTM D3479

Fatigue is the weakening of a material caused by repeated application of load. It is progressive and localized structural damage that occurs when a material is subjected to cyclic loading. Fatigue testing is carried out in order to assess the performance of a material under similar conditions of real-world use. Fatigue damage occurs when a material is subjected to repeated loading and unloading. If the loads are above a certain threshold, microscopic cracks will begin to form. The nominal maximum stress values that cause such damage may be much less than the strength of the material typically quoted as the ultimate tensile stress limit (Tm). The ability to detect fatigue damage is an important advantage as fatigue is one of the major reasons of in-service failure of materials.

Specimens were subject to tensile fatigue testing according to ASTM D3479 method. This test method is designed to yield tensile fatigue data for material specifications, research and development, quality assurance, and structural design and analysis. This test method can be utilized in the study of fatigue damage in a polymer matrix composite such as the occurrence of microscopic cracks, fiber fractures, or delaminations. Tensile fatigue specimens were cut to size according to ASTM D3479 (length 150 mm; width 25 mm). The mechanical tests were performed using MTS Landmark 100 kN. The untested specimen showed no significant fluorescence when viewed under a fluorescence detector.

Figure 3:
FIG. 3(a) shows images at the fluorescence microscope of an untested specimen (b) and a tested specimen subject to 100,000 cycles of Stress=60% Tm (ultimate tensile strength) (all at 10× magnification).
Figure 3:
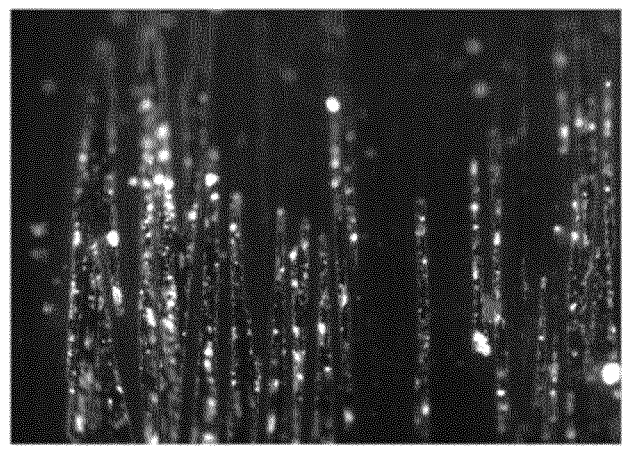

The specimen was subjected to 100000 cycles under 60% of the ultimate tensile strength (Tm) with a frequency of 10 Hz. A 40% of stiffness drop was observed and fluorescence was observed along the entire length of the specimen, either in the 90°-direction or in the 0°-direction of the fibres (FIG. 3).

Discussion of the Results

The specimens of composite material comprising the agent have been tested under traction, compression and fatigue, according to the methods and procedures described herein.

The untested specimen was first analyzed under the fluorescence microscope and no fluorescence was detected. This indicates that the fluorescent compound and the quencher compound are complexed with curcubituril.

Tensile Stress Test

When the specimen is stressed at 70% Tm (i.e., at 70% of the ultimate tensile strength for that specific material) the fluorescence of the material is detected under the fluorescence microscope. This indicates that the mechanical stress can be detected in the material before microcracks start to form in the material.

The fluorescence increases to a maximum when the specimen is broken.

Compression Stress Test

The specimen was tested under compression. Also under compression test the fluorescence appear at 70% Tm, well before final breaking of the specimen.

Fatigue Stress Tests

A testes specimen subject to 100000 cycles of stress at 60% Tm (i.e. at 60% of the ultimate tensile strength, the fluorescence of the material is detected under the fluorescence indicating that the material is irreversibly stressed.

Measurement Methods $^1$H-NMR was measured using a Bruker AVANCE 300 (300 MHz) or a Bruker AVANCE 400 (400 MHz) spectrometer at 25° C. All chemical shifts (δ) were reported in ppm relative to the proton resonances resulting from the incomplete deuteration of the NMR solvents. All chemical shifts (δ) were reported in ppm relative to the carbon resonances of the NMR solvents.

Electrospray Ionization Mass Spectrometry (ESI-MS): ESI-MS experiments were performed on a Waters ZMD spectrometer equipped with an electrospray interface.

REFERENCES

Biedermann, F., Elmalem, E., Ghosh, I., Nau, W. M., & Scherman, O. A. (2012). Strongly fluorescent, switchable perylene bis(diimide) host-guest complexes with Cucurbituril[8], in water. Angewandte Chemie—International Edition, 51(31), 7739-7743.

Früh, A. E., Artoni, F., Brighenti, R., & Dalcanale, E. (2017). Strain Field Self-Diagnostic Poly(dimethylsiloxane) Elastomers. Chemistry of Materials, 29(17), 7450-7457.

ASTM D3039/D3039M-17, Standard Test Method for Tensile Properties of Polymer Matrix Composite Materials, ASTM International, West Conshohocken, PA, 2017, www.astm.org;

ASTM D3410/D3410M-16, Standard Test Method for Compressive Properties of Polymer Matrix Composite Materials with Unsupported Gage Section by Shear Loading, ASTM International, West Conshohocken, PA, 2016, ASTM D3479/D3479M-12, Standard Test Method for Tension-Tension Fatigue of Polymer Matrix Composite Materials, ASTM International, West Conshohocken, PA, 2012,

The invention claimed is:

1. An agent to detect stress or fatigue in a composition, the agent comprising:
   Cucurbituril[8];
   a fluorescent compound having an emission in a wave length of above 400 nm; and
   a quencher compound;
   wherein the fluorescent compound has at least one reactive group and the quencher compound has at least one reactive group, the at least one reactive group of the fluorescent compound and the at least one reactive group of the quencher compound are the same or different and comprise one or more of —OH, a primary amine, a secondary amine, and carboxylic anhydride.

2. The agent of claim 1, wherein a molar excess of the quencher compound is present with respect to equimolar amounts of Cucurbituril[8] and the fluorescent compound.

3. The agent of claim 1, wherein the at least one reactive group of the fluorescent compound and the at least one reactive group of the quencher compound are the same or different and comprise a primary amine or a secondary amine.

4. The agent of claim 1, wherein the fluorescent compound is a compound of formula (I)

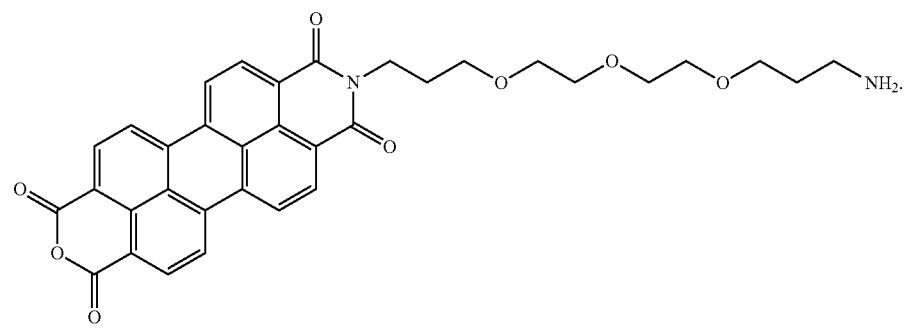

(I)

5. The agent of claim 1, wherein the quencher compound is a compound of formula (II) or (III)

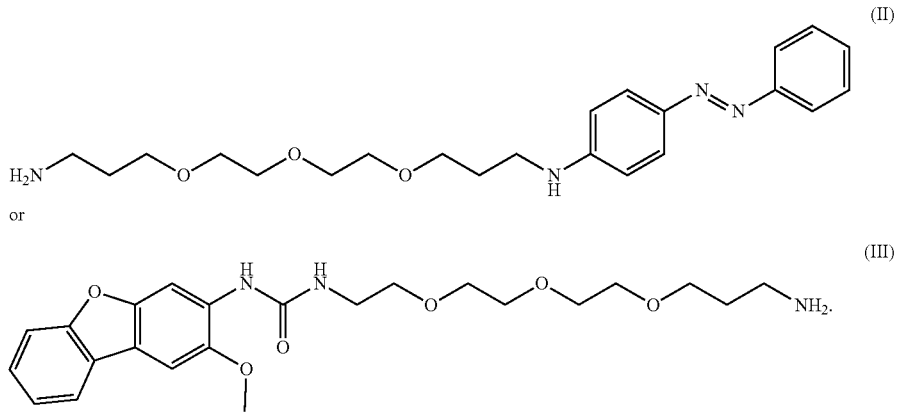

6. A composition comprising:
an agent comprising:
Cucurbituril[8];
a fluorescent compound having an emission in a wave length of above 400 nm; and
a quencher compound;
wherein the fluorescent compound has at least one reactive group and the quencher compound has at least one reactive group, the at least one reactive group of the fluorescent compound and the at least one reactive group of the quencher compound are the same or different and comprise one or more of —OH, a primary amine, a secondary amine, and carboxylic anhydride;
a resin comprising groups; and
a curing agent comprising reactive groups,
wherein the reactive groups of the curing agent are the same as the reactive groups of the agent, and the groups of the resin react with the reactive groups of the agent and the reactive groups of the curing agent.

7. The composition of claim 6, wherein the resin comprises an epoxy group, a hydroxyl group, a polyhydroxyl group, or an isocyanate group.

8. A cured composition obtained by reacting the composition of claim 6.

9. The cured composition of claim 8 further comprising secondary or tertiary amine groups.

10. The cured composition of claim 8, further comprising one or more fibres.

11. Process A process for producing a cured composition, the process comprising:
curing a mixture comprising a resin, a curing agent, and an agent comprising:
Cucurbituril[8];
a fluorescent compound having an emission in a wave length of above 400 nm; and
a quencher compound;
wherein the fluorescent compound has at least one reactive group and the quencher compound has at least one reactive group, the at least one reactive group of the fluorescent compound and the at least one reactive group of the quencher compound are the same or different and comprise one or more of —OH, a primary amine, a secondary amine, and carboxylic anhydride.

12. A method for detecting one or more of stress and fatigue in a composite material, the process comprising:
exposing the composite material to electromagnetic radiation, the composite material comprising a cured form of a composition comprising the agent according to claim 1; and
observing whether the exposed composite material exhibits fluorescence.

13. A method for detecting one or more of stress and fatigue in a thermosetting polymer, the process comprising:
exposing the thermosetting polymer to electromagnetic radiation, the thermosetting polymer comprising a cured form of a composition comprising the agent according to claim 1; and
observing whether the exposed thermosetting polymer exhibits fluorescence.

14. A method for detecting one or more of stress and fatigue in an epoxy resin composite, the process comprising:
exposing the epoxy resin composite to electromagnetic radiation, the epoxy resin composite comprising a cured form of a composition comprising the agent according to claim 1; and
observing whether the exposed epoxy resin composite exhibits fluorescence.

* * * * *